United States Patent [19]
Lucarelli et al.

[11] Patent Number: 5,412,132
[45] Date of Patent: May 2, 1995

[54] COPOLYMERS OF ISOCYANATO SILICONES AND PLASTICS WHICH CONTAIN ACTIVE HYDROGEN SUBSTITUENTS

[75] Inventors: Michael A. Lucarelli, Mattoon, Ill.; William J. Raleigh, Rensselaer; Larry N. Lewis, Scotia, both of N.Y.

[73] Assignee: General Electric Company, Waterford, N.Y.

[21] Appl. No.: 234,492

[22] Filed: Apr. 28, 1994

Related U.S. Application Data

[63] Continuation of Ser. No. 989,684, Dec. 14, 1992, abandoned.

[51] Int. Cl.⁶ ............................ C07F 7/08; C07F 7/10
[52] U.S. Cl. ...................................... 556/414; 528/26; 528/28; 528/29
[58] Field of Search .................... 556/414; 528/26, 28, 528/29

[56] References Cited

U.S. PATENT DOCUMENTS

| | | | |
|---|---|---|---|
| 3,170,891 | 2/1965 | Speier | 556/414 X |
| 3,179,713 | 4/1965 | Brown | 556/414 X |
| 4,478,893 | 10/1984 | Schonfelder et al. | 556/414 X |
| 4,668,754 | 5/1987 | Policastro et al. | 528/26 |
| 4,678,513 | 7/1987 | Bagaglio et al. | 106/38.22 |
| 4,766,185 | 8/1988 | Ryntz et al. | 525/479 |
| 4,785,067 | 11/1988 | Brumbill | 528/26 |
| 4,822,850 | 4/1989 | Yashuda et al. | 556/414 X |
| 4,847,319 | 7/1989 | Bandlish | 524/589 |
| 4,935,482 | 6/1990 | Decker et al. | 528/28 |
| 5,057,377 | 10/1991 | Karydas et al. | 428/447 |
| 5,096,994 | 3/1992 | Schmalsteig et al. | 556/414 X |

OTHER PUBLICATIONS

C. A. Dexter et al., "m-TMI, A Novel Unsaturated Aliphatic Isocyanate," J. Coat. Tech., reprint, v. 58, n. 737, pp. 43–47 (1986).

IMI ® (META) unsaturated aliphatic isocyanate, American Cyanamid Company product information sheet, 1988.

C. C. Zhou et al., "Siloxanes with aliphatic isocyanate groups," Polymer Bulletin, 22, 85–88 (1989).

*Primary Examiner*—Paul F. Shaver

[57] ABSTRACT

A novel isocyanato-endcapped siloxane compound and a method of preparation are disclosed, and which can be further copolymerized with a variety of thermoplastic resins containing active hydrogen substituents such as polycarbonates and polyphenylene ethers.

20 Claims, No Drawings

COPOLYMERS OF ISOCYANATO SILICONES AND PLASTICS WHICH CONTAIN ACTIVE HYDROGEN SUBSTITUENTS

This is a continuation of application Ser. No. 07/989,684 filed on Dec. 14, 1992, now abandoned.

The present invention relates to novel modified silicone fluids. More particularly, the present invention relates to novel silicone fluids modified with hydrocarbyl isocyanato groups. The present invention further relates to copolymers or polymers containing active hydrogen substituents and the alkenyl isocyanato modified silicones.

BACKGROUND OF THE PRESENT INVENTION

Copolymers of polysiloxanes and other thermoplastic resins have found wide utility in commercial applications. For example, it is known in the art that polycarbonates can be copolymerized with linear polysiloxanes which are modified with allyl phenolic endgroups. These organopolysiloxane polycarbonate copolymers are disclosed in Vaughn, Jr., U.S. Pat. Nos. 3,419,634 and 3,419,635. Due to the usefulness of such copolymers, new methods for preparing siloxane copolymers are continuously sought after.

Zhou et al., Polymer Bulletin 22, 85–88 (1989) describe the hydrosilation of an alkenyl isocyanate onto cyclic siloxanes containing SiH groups, such as 1,3,5,7-tetramethylcyclotetrasiloxane. However, long reaction times are necessary and poor yields are obtained.

It has now been discovered that novel siloxanes which are endcapped with isocyanate functionalities can be easily prepared and are useful in producing siloxane copolymers with thermoplastics containing alcohol and/or amine substituents. Further, the copolymerization produces no reaction by-products.

SUMMARY OF THE PRESENT INVENTION

According to the present invention there is provided a composition comprising units of the formulae: M'M; M'M'; M'D$_x$M; and M'D$_x$M' wherein M represents a monofunctional siloxane of the formula R$_3$SiO$_{\frac{1}{2}}$; M' represents a monofunctional siloxane of the formula R'$_a$R$_b$SiO$_{\frac{1}{2}}$; D represents a difunctional siloxane of the formula R$_2$SiO$_{2/2}$; each R is the same or different and independently represents a substituted or unsubstituted monovalent hydrocarbon of from about 1 to about 30 carbon atoms; each R' is the same or different and independently represents an alkenyl isocyanato radical; "a" is an integer of 1, 2 or 3; "b" is an integer of 0, 1 or 2; a+b=3; and "x" is an integer of above about 1.

Also according to the present invention, there is provided a process for producing the compositions of the present invention comprising reacting the corresponding monofunctional hydride siloxane with an alkenyl isocyanate compound in the presence of a hydrosilation catalyst. The preferred alkenyl isocyanate compound is 1-(1-isocyanato-1-methylethyl)-3-(1-methylethenyl)-benzene also known as, meta-isopropenyl-α,α-dimethyl benzyl isocyanate.

The present invention further provides copolymers of the siloxanes of the present invention with thermoplastic resins containing alcohol and/or amine substituents.

DETAILED DESCRIPTION OF THE PRESENT INVENTION

The present invention provides novel isocyanato endcapped siloxane polymers which are useful as reactive polymers and may be employed in preparing siloxane copolymers with thermoplastic resins having active hydrogen substituents to provide improved impact properties and reduced smoke density upon burning.

Particularly useful isocyanato-endcapped siloxanes of the present invention are those generally comprising units of the formulae:

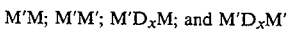

In the above formula

M represents a monofunctional siloxane of the formula R$_3$SiO$_{\frac{1}{2}}$;

M' represents a monofunctional siloxane of the formula R'$_a$R$_b$SiO$_{\frac{1}{2}}$; and D represents a difunctional siloxane of the formula R$_2$SiO$_{2/2}$.

Each R is the same or different and independently represents a substituted or unsubstituted monovalent hydrocarbon of from about 1 to about 30 carbon atoms. Illustratively, R typically contains no more than eight carbon atoms, and is selected from, but not limited to, those such as substituted or unsubstituted alkyl radicals, e.g., methyl, ethyl and isopropyl; cycloaliphatic radicals, e.g., cyclopentyl and cyclohexenyl; alkenyl radicals, e.g., vinyl and allyl; aryl radicals, e.g., benzyl and phenyl; alkaryl and aralkyl groups. In preferred embodiments of the present invention, all of the R groups represent a methyl group.

Each R' is the same or different and independently represents an alkenyl isocyanato radical. Illustratively, R' is 1-(1-isocyanato-1-methylethyl)-3-(1-methylethenyl)-benzene.

"a" is an integer of 1, 2 or 3; "b" is an integer of 0, 1 or 2; provided a+b=3.

"x" is an integer of above about 1, and typically ranges from about 1 to about 1000, more preferably from about 1 to about 100, and most preferably from about 1 to about 20.

Particularly useful compositions of the present invention comprise those of the formulae:

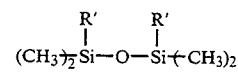

and

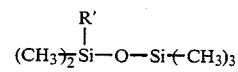

wherein R' is 1-(1-isocyanato-1-methylethyl)-3-(1-methylethenyl)-benzene.

The novel isocyanato silicones of the present invention are generally prepared by hydrosilylating the appropriate linear or branched siloxane with an alkenyl isocyanate.

The silicone hydrides for use in the practice of the present invention are typically those which correspond to the product isocyanato siloxanes, and are generally selected from

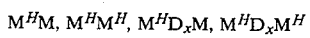

or combinations of any of the foregoing wherein $M^H$ is a monofunctional siloxane hydride of the formula $(R)_2(H)SiO_{\frac{1}{2}}$ and R, D, M and x are as above defined. The monofunctional siloxane hydrides are available commercially and can be prepared by methods known to those skilled in the art.

The alkenyl isocyanate compounds useful in the present invention can be any compound comprising both a functional reactive alkenyl group and a isocyanate functional group. Such compounds are well known to those skilled in the art. A particularly useful alkenyl isocyanate compound is 1-(1-isocyanato-1-methylethyl)-3(1-methylethenyl)-benzene of the formula:

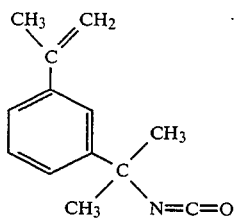

This compound is described in the literature and is commercially available as TMI® from American Cyanamid Company. See, inter alia, Dexter et al., "m-TMI, A Novel Unsaturated Aliphatic Isocyanate," Journal of Coatings Technology, v. 5, n. 737, pp. 43–47 (June 1986); and TMI® (META) unsaturated aliphatic isocyanate brochure, American Cyanamid Company.

The monofunctional siloxane hydride and the alkenyl isocyanate compound are typically mixed in the presence of an inert solvent prior to reaction. Particularly useful as a solvent are the normally liquid aliphatic, cycloaliphatic or aromatic hydrocarbon or halogenated hydrocarbon compounds of from about 6 to about 15 carbon atoms. These include, but are not limited to, n-heptane, cycloheptane, n-hexane, cyclohexane, benzene, toluene, xylene, styrene, mesitylene, naphthene, methylene chloride and mixtures thereof. The hydrocarbon solvent may also comprise polyalpha-olefins and mineral oils such as mineral spirits.

The monofunctional siloxane hydride and the alkenyl isocyanate are then generally reacted by hydrosilation techniques well known to those of ordinary skill in the art. In general the hydrosilation reaction proceeds in the presence of a Group VIII precious metal complex, i.e. platinum, rhodium and/or ruthenium complexes. Such catalyst complexes are well described in the patent literature, e.g., Karstedt, U.S. Pat. No. 3,775,452; Ashby et al., U.S. Pat. No. 4,288,345; Bailey et al., U.S. Pat. No. 3,336,239; Ashby, U.S. Pat. No. 4,421,903; Lamoreaux, U.S. Pat. No. 3,220,972; and Lewis, U.S. Pat. No. 4,946,818. See also, J. Organometallic Chem. 408 (1991) pp. 297–304. Preferred are the platinum based catalysts described in above-mentioned Lamoreaux and Karstedt patents. Other useful catalysts may include complexes of tertiary amines with cuprous chloride.

The reaction proceed at temperatures ranging from about 50° C. to about 150° C. and pressures ranging from about 1 atm to about 5 atm for a period of time of from about 1 hour to about 5 hours. The ratio of reagents ranges from 1:1, moles isocyanate:moles siloxane hydride, to potentially excess siloxane hydride.

The product isocyanato endcapped siloxane is then purified from the inert solvent by standard distillation techniques. The isocyanato siloxane can then be used as a reactive additive or can be copolymerized with copolymerizate thermoplastic resins containing alcohol and/or amine substituents to provide the novel copolymers of the present invention.

Useful thermoplastic copolymerizates having alcohol and/or amine substituents are those such as polycarbonates, polyphenylene ethers, polyols and polyamines. Copolymerization occurs between the isocyanate group on the siloxane and the active hydrogen, i.e., hydroxy or amine, present in the copolymerizate, by the formation of a urethane or urea linkage, respectively.

The copolymerization is described below with regard to polycarbonate, however, any thermoplastic containing an active alcohol or amine substituent may be employed, such as polyphenylene ethers.

The polycarbonates useful in the practice of the present invention are well known to those skilled in the art and can comprise non-aromatic as well as aromatic forms.

With respect to aromatic polycarbonates, these can be made by those skilled in this art or they can be obtained from a variety of commercial sources. They may be prepared by reacting a dihydric phenol with a carbonate precursor, such as phosgene, a haloformate or carbonate ester. Typically they will have recurring structural units of the formula:

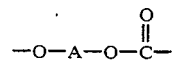

wherein A is a divalent aromatic radical of the dihydric phenol employed in the polymer producing reaction. Preferably, the aromatic carbonate polymers have an intrinsic viscosity ranging from 0.30 to 1.0 dl/g (measured in methylene chloride at 25° C.). By dihydric phenols is meant mononuclear or polynuclear aromatic compounds containing two hydroxy radicals, each of which is attached to a carbon atom of an aromatic nucleus. Typically, dihydric phenols include 2,2-bis(4-hydroxyphenyl)propane; 2,2-bis(3,5-dimethyl-4-hydroxyphenyl)propane; 4,4'-di-hydroxydiphenyl ether; bis(2-hydroxyphenyl)methane, mixtures thereof and the like. The preferred aromatic carbonate polymer is a homopolymer derived from 2,2-bis(4-hydroxyphenyl)propane or bisphenol-A.

The isocyanate-endcapped siloxane is merely added to the polycarbonate resin, in either a solvent or the liquified resin, and the reaction proceeds by the interaction of the isocyanate with the hydroxy group of the polycarbonate, polyphenylene ether or polyol, or the amine group of the polyamine, as is known to those skilled in the art. See, e.g., J. H. Saunders, Rubber Chem. & Tech., v. XXXIII, n. 5, December 1960, pp. 1293–94. In the case of a solventless system, the reaction would not produce any waste or by-product since all reagents could combine to form the desired product. The resulting copolymers can then be molded into a wide variety of useful commercial products.

DESCRIPTION OF THE PREFERRED EMBODIMENTS

The following examples are presented for illustrative purposes only. They are not to be construed to limit the scope of the appended claims in any manner whatsoever.

COMPARATIVE EXAMPLE A

ATTEMPTED HYDROSILYLATION BETWEEN $D^H_4$ AND TMI 10 g (49.8 mmol) of TMI was combined with the platinum-octanol catalyst described by Lamoreaux (U.S. Pat. No. 3,220,972)(35 μL of 3.5% Pt by weight solution) in 50 mL mesitylene. Then 3 g (50mmol/SiH) $D^H_4$ was added and the mixture was refluxed for 13 hours. Analysis by gas chromatography showed no conversion of starting materials occurred. The reaction was repeated by reversing the order of addition of reagents so that $D^H_4$ was combined with platinum catalyst, this time as described by Karstedt, diplatinum tris(divinyl tetramethyl disiloxane (U.S. Pat. No. 3,775,452)(3.5 μL of 5% Pt by weight in xylene) in mesitylene, followed by addition of TMI. Again, no trace of product was observed.

EXAMPLE 1

Reaction of TMI with $M^H M^H$. 10 g (49.6 mmol) of TMI and 6.6 g (49.2 mmol) of $M^H M^H$ were combined in 50 mL toluene. To the mixture is then added Karstedt platinum catalyst (40 μL of a 5% Pt solution in xylene). The mixture was refluxed for 3 days, at which point gas chromatography analysis showed 66% conversion to products had occurred. The product

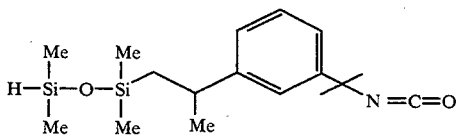

where Me represents methyl, was isolated in about 45% yield by distillation, 0.3 mm, 103°–108° C.

Analysis by $^1H$ NMR spectroscopy showed: −0.02 (s 6H), 0.22 (s, 6H), 1.01 (d, J=7Hz, 2H), 1.32 (d, J=7Hz, 3H), 1.74 (s, 6H), 2.98 (m, 1H), 4.70 (m, 1H), 7.2 (m, 4H).

EXAMPLE 2

Reaction of TMI with $M^H M$. 10 g (49.6 mmol) of TMI and 10.0 g (56.8 mmol) of $M^H M$ were combined in 50 mL toluene. To the mixture is then added Karstedt platinum catalyst (40 μL of a 5% Pt solution in xylene). The mixture was refluxed for 13 hours, at which point gas chromatography analysis showed greater than 90% conversion to products had occurred. The product

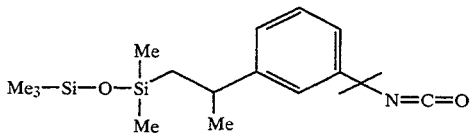

where Me represents methyl was purified by distillation, 0.4 mm, 103°–108° C.

Analysis by $^1H$ NMR spectroscopy showed: −0.02 (s 6H), 0.11 (s, 9H), 1.01 (d, J=7Hz, 2H), 1.34 (d, J=7Hz, 3H), 1.76 (s, 6H), 2.98 (m, 1H), 7.2 (m, 4H). Analysis of $^{13}C$ NMR spectroscopy showed 0.85 (SiCH$_3$), 2.00 (SiCH$_3$), 26.00 (CH$_3$), 28.54 (CH$_2$), 33.10 (CH$_3$), 35.91 (CH), 60.89 (c, quat), 121.72 (aromatic CH), 122.81 (aromatic CH), 125.46 (aromatic CH), 128.39 (aromatic CH), 150.17 (c, quat). Infra red spectroscopy showed 2262 cm$^{-1}$ν$_{co}$. Other major peaks, 2959 cm$^{-1}$, 1256 cm$^{-1}$, 1057 cm$^-$, 841 cm$^{-1}$, 817 cm$^{-1}$, 799 cm$^{-1}$, 470 cm$^{-1}$. High resolution GCMS calculated C$_{18}$H$_{31}$NOSi$_2$ 349.1893. Found 349.1883.

The above-mentioned patents and publications are hereby incorporated by reference.

Many variations of the present invention will suggest themselves to those skilled in the art in light of the above-detailed description. For example, any siloxane can be employed which is endcapped with the isocyanate compound, such as those of the formulae M'D$_x$M and M'D$_x$M'. Further, other compounds having both alkenyl and isocyanate functionalities can be employed in addition to 1-(1-isocyanato-1-methylethyl)-3-(1-methylethenyl)-benzene. The isocyanate functional silicones can then be reacted with hydroxy or amine containing compounds such as polycarbonates, polyphenylene ethers, polyols and polyamines. All such obvious modifications are within the full intended scope of the present invention.

It is claimed:

1. A composition comprising units of the formula:

M'M

M'M'

M'D$_x$M

M'D$_x$M' wherein
   M represents a monofunctional siloxane of the formula R$_3$SiO$_{\frac{1}{2}}$;
   M' represents a monofunctional siloxane of the formula R'$_a$R$_b$SiO$_{\frac{1}{2}}$;
   D represents a difunctional siloxane of the formula R$_2$SiO$_{2/2}$;
   each R is the same or different and independently represents a substituted or unsubstituted monovalent hydrocarbon of from about 1 to about 30 carbon atoms;
   said R' comprises 1-(1-isocyanato-1-methylethyl)-3-(1-methylethenyl)benzene;
   "a" is a integer of 1, 2 or 3;
   "b" is an integer of 0, 1 or 2;
   a+b=3; and
   x is an integer of above about 1.

2. A composition as defined in claim 1 wherein each R is the same or different and is selected from alkyl, cycloalkyl, alkenyl, aryl, alkaryl, aralkyl groups.

3. A composition as defined in claim 2 wherein each R represents a methyl group.

4. A composition as defined in claim 1 wherein x ranges from about 1 to about 1000.

5. A composition as defined in claim 1 wherein x ranges from about 1 to about 20.

6. A composition as defined in claim 1 comprising

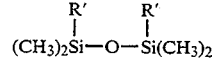

wherein each R' represents meta-isopropyl-α,α-dimethyl benzyl isocyanate.

7. A composition as defined in claim 1 comprising

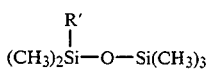

wherein R' represents meta-isopropyl-α,α-dimethyl benzyl isocyanate.

8. A process for preparing a composition comprising units of the formula:

M'M

M'M'

M'D$_x$M

M'D$_x$M' wherein
M represents a monofunctional siloxane of the formula R$_3$SiO$_{\frac{1}{2}}$;
M' represents a monofunctional siloxane of the formula R'$_a$R$_b$SiO$_{\frac{1}{2}}$;
D represents a difunctional siloxane of the formula R$_2$SiO$_{2/2}$;
each R is the same or different and independently represents a substituted or unsubstituted monovalent hydrocarbon of from about 1 to about 30 carbon atoms;
said R' comprises 1-(1-isocyanato-1-methylethyl)-3-(1-methylethenyl)benzene;
"a" is a integer of 1, 2 or 3;
"b" is an integer of 0, 1 or 2;
a+b=3; and
x is an integer of above about 1.
said process comprising:
mixing the corresponding monofunctional hydride siloxane of the formulae:

M$^H$M

M$^H$M$^H$

M$^H$D$_x$M

M$^H$D$_x$M$^H$ with 1-(1-isocyanato-1-methylethyl)-3-(1-methylethenyl)-benzene;
and reacting said monofunctional hydride siloxane and 1-(1-isocyanato-1-methylethyl)-3-(1-methylethenyl)-benzene in the presence of a hydrosilation catalyst.

9. A process as defined in claim 8 wherein each R is the same or different and is selected from alkyl, cycloalkyl, alkenyl, aryl, alkaryl, aralkyl groups.

10. A process as defined in claim 9 wherein each R represents a methyl group.

11. A process as defined in claim 8 wherein x ranges from about 1 to about 1000.

12. A process as defined in claim 8 wherein x ranges from about 1 to about 20.

13. A process as defined in claim 8 wherein said monofunctional siloxane hydride comprises

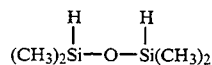

and said alkenyl isocyanate comprises meta-isopropyl-α,α-dimethyl benzyl isocyanate.

14. A process as defined in claim 8 wherein said monofunctional siloxane hydride comprises

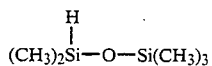

and said alkenyl isocyanate comprises meta-isopropyl-α,α-dimethyl benzyl isocyanate.

15. A process as defined in claim 8 wherein said mixing step is conducted in the presence of a solvent selected from normally aliphatic, cycloaliphatic or aromatic hydrocarbon or halogenated hydrocarbon compounds of from about 6 to about 15 carbon atoms.

16. A process as defined in claim 8 wherein said catalyst comprises a platinum octanol catalyst, a diplatinum tris(divinyl tetramethyl siloxane) catalyst or an amine cuprous chloride complex.

17. A siloxane copolymer comprising units derived from
an isocyanate endcapped siloxane comprising units of the formula:

M'M

M'M'

M'D$_x$M

M'D$_x$M' wherein
M represents a monofunctional siloxane of the formula R$_3$SiO$_{\frac{1}{2}}$;
M' represents a monofunctional siloxane of the formula R'$_a$R$_b$SiO$_{\frac{1}{2}}$;
D represents a difunctional siloxane of the formula R$_2$SiO$_{2/2}$;
each R is the same or different and independently represents a substituted or unsubstituted monovalent hydrocarbon of from about 1 to about 30 carbon atoms;
each R' is 1-(1-isocyanato-1-methylethyl)-3-(1-methylethenyl)-benzene;
"a" is an integer of 1, 2 or 3;
"b" is an integer of 0, 1 or 2;
a+b=3; and
x is an integer of above about 1; and
a copolymerizate having alcohol and/or amine substituents.

18. A copolymer as defined in claim 17 wherein said copolymerizate is selected from polycarbonates, polyphenylene ethers, polyols, polyamines and mixtures of any of the foregoing.

19. A copolymer as defined in claim 18 wherein said copolymerizate comprises poly(bisphenol A)carbonate.

20. A composition consisting essentially of units of the formula:

M'M

M'M'

M'D$_x$M

M'D$_x$M' wherein

M represents a monofunctional siloxane of the formula R$_3$SiO$_{\frac{1}{2}}$;

M' represents a monofunctional siloxane of the formula R'$_a$R$_b$SiO$_{\frac{1}{2}}$;

D represents a difunctional siloxane of the formula R$_2$SiO$_{2/2}$;

each R is the same or different and independently represents a substituted or unsubstituted monovalent hydrocarbon of from about 1 to about 30 carbon atoms;

each R' is 1-(1-isocyanato-1-methylethyl)-3-(1-methylethenyl)-benzene;

"a" is an integer of 1, 2 or 3;

"b" is an integer of 0, 1 or 2;

a+b=3; and x is an integer of above about 1.

* * * * *